United States Patent
Nishio et al.

(10) Patent No.: US 9,282,976 B2
(45) Date of Patent: Mar. 15, 2016

(54) REMOTE-CONTROLLED ACTUATOR ASSEMBLY

(75) Inventors: Yukihiro Nishio, Iwata (JP); Yoshitaka Nagano, Iwata (JP)

(73) Assignee: NTN CORPORATION, Osaka (JP)

( * ) Notice: Subject to any disclaimer, the term of this patent is extended or adjusted under 35 U.S.C. 154(b) by 738 days.

(21) Appl. No.: 13/582,819

(22) PCT Filed: Mar. 3, 2011

(86) PCT No.: PCT/JP2011/054854
§ 371 (c)(1),
(2), (4) Date: Sep. 5, 2012

(87) PCT Pub. No.: WO2011/108623
PCT Pub. Date: Sep. 9, 2011

(65) Prior Publication Data
US 2012/0325508 A1 Dec. 27, 2012

(30) Foreign Application Priority Data
Mar. 5, 2010 (JP) .................................. 2010-048645

(51) Int. Cl.
| | |
|---|---|
| *B23B 45/00* | (2006.01) |
| *A61B 17/16* | (2006.01) |
| *B23B 39/14* | (2006.01) |

(52) U.S. Cl.
CPC ......... *A61B 17/1617* (2013.01); *A61B 17/1626* (2013.01); *B23B 39/14* (2013.01); *B23B 45/005* (2013.01); *A61B 17/1624* (2013.01); *A61B 17/1628* (2013.01); *A61B 17/1631* (2013.01); *A61B 17/1642* (2013.01)

(58) Field of Classification Search
CPC .... B23B 45/00; B23B 39/14; A61B 17/1626; A61B 17/1631; A61B 17/16
USPC .............................. 173/20; 74/422, 519, 469
See application file for complete search history.

(56) References Cited

U.S. PATENT DOCUMENTS

| | | | |
|---|---|---|---|
| 4,265,231 | A | 5/1981 | Scheller, Jr. et al. |
| 4,466,429 | A | 8/1984 | Loscher et al. |

(Continued)

FOREIGN PATENT DOCUMENTS

| | | | |
|---|---|---|---|
| JP | 2010-046764 | 3/2010 | |
| JP | 2010-046197 | 3/2011 | |
| WO | WO 2010029741 A1 * | 3/2010 | .............. B23B 45/00 |

OTHER PUBLICATIONS

English Translation of the International Preliminary Report on Patentability issued Oct. 11, 2012 in corresponding International Patent Application No. PCT/JP2011/054854.

(Continued)

*Primary Examiner* — Michelle Lopez

(57) ABSTRACT

A remote-controlled actuator assembly includes a guide section (3) of an elongated shape, a distal end member (2) fitted to a tip end of the guide section for alteration in attitude, an operating tool (1) in the distal end member, and a restraining tool (6) for aligning the distal end member straight with the guide section. The distal end member is altered in attitude through advancing/retracting attitude altering members (31) in the guide section by attitude altering drive sources (43), which are controlled by an attitude control unit (62). An advance or retraction position detector (45) detects an advance/retraction position of the attitude altering members while the attitude altering members applying a preload to the distal end member restrained by the restraining tool. The attitude control unit uses the detection value as information on the advance/retraction position corresponding to an initial position-attitude of the distal end member.

9 Claims, 8 Drawing Sheets

(56) References Cited

U.S. PATENT DOCUMENTS

| | | | |
|---|---|---|---|
| 8,439,899 B2 * | 5/2013 | Nishio | A61B 17/1626 606/1 |
| 2011/0138962 A1 | 6/2011 | Ozaki et al. | |

OTHER PUBLICATIONS

International Search Report of Corresponding PCT Application PCT/JP2011/054854 mailed Mar. 29, 2011.

* cited by examiner

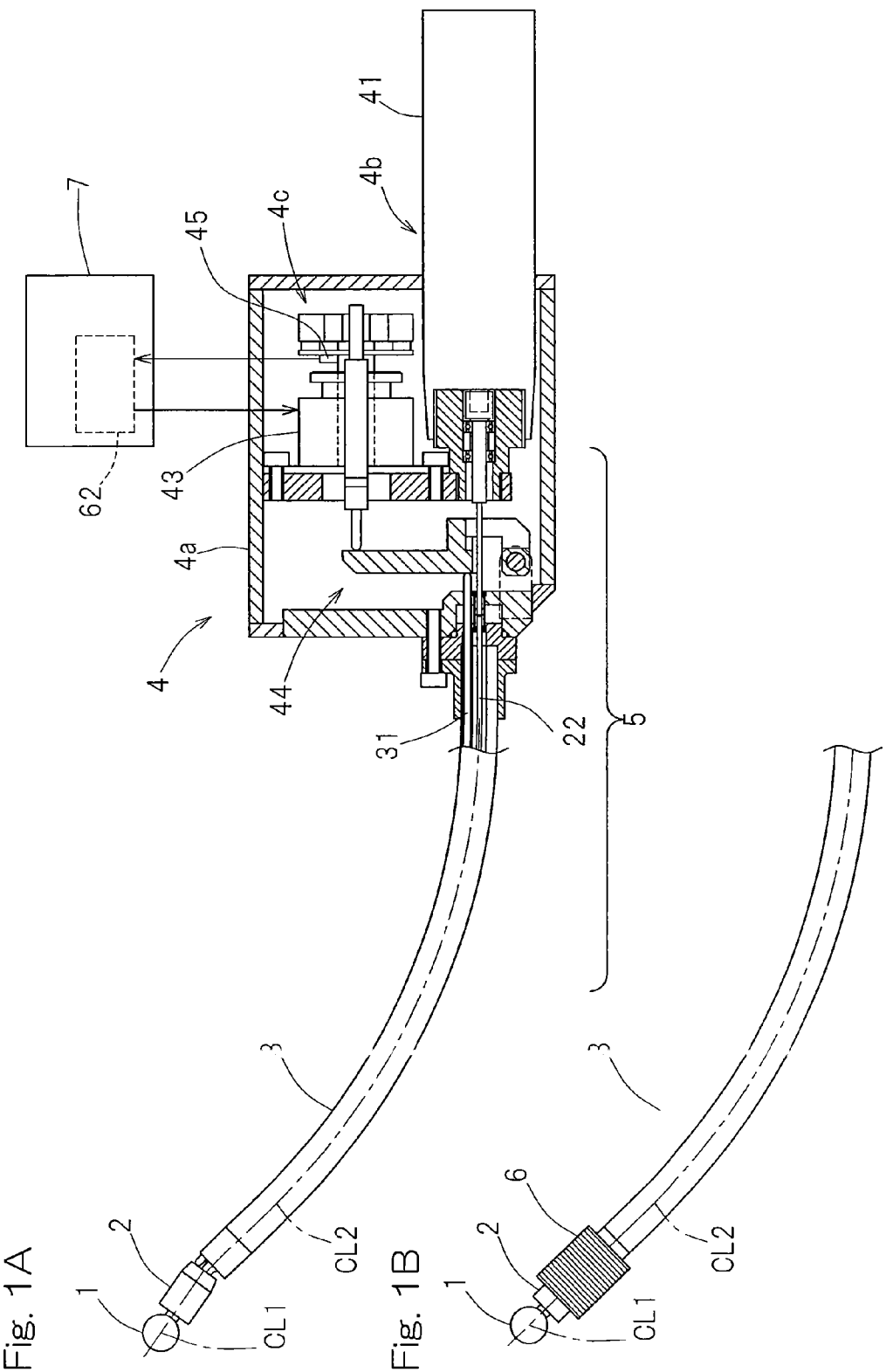

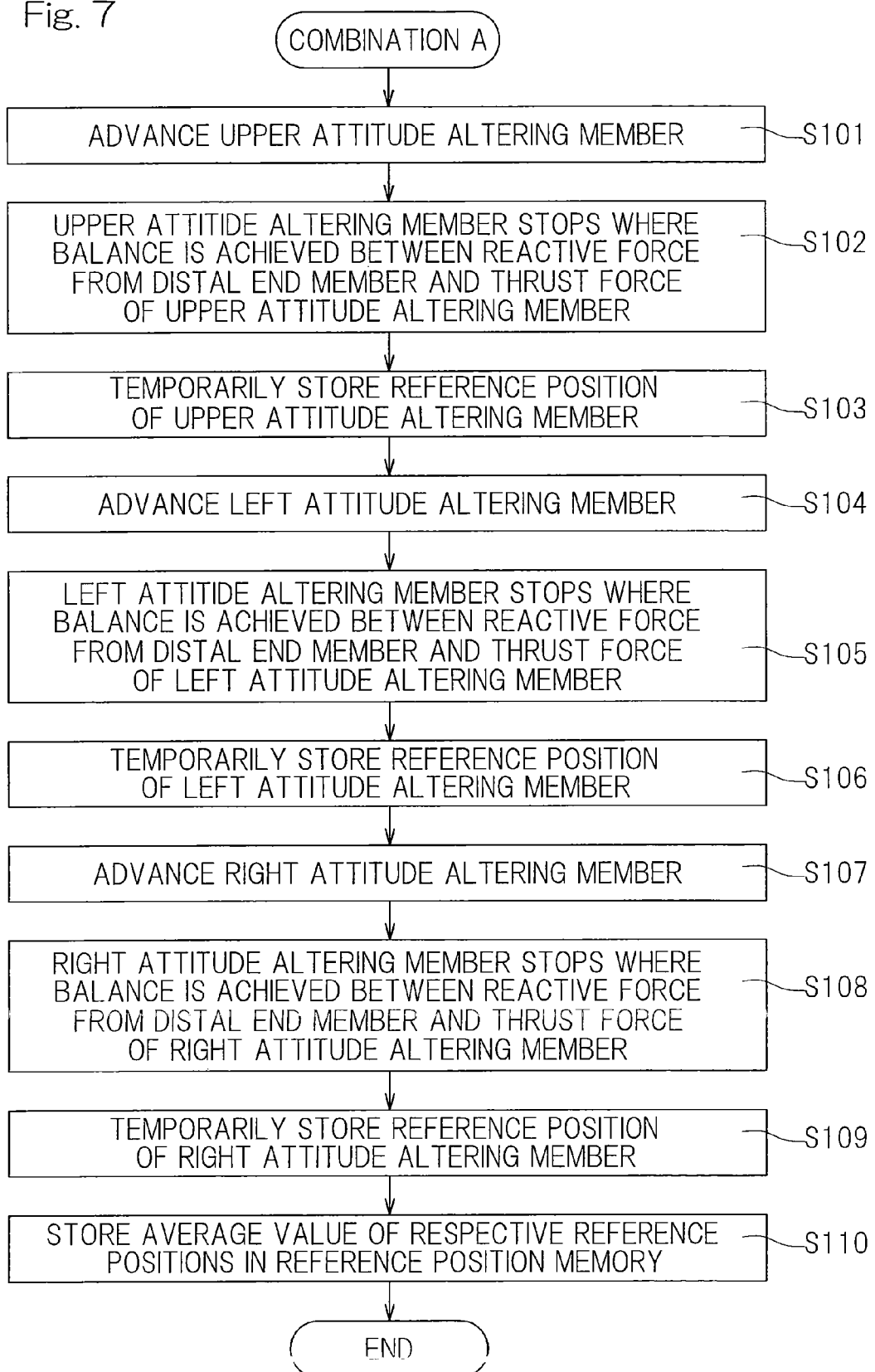

PRIOR ART

REMOTE-CONTROLLED ACTUATOR ASSEMBLY

CROSS REFERENCE TO THE RELATED APPLICATIONS

This application is a U.S. National Phase application of PCT/JP2011/054854 filed Mar. 3, 2011 and claims the priority benefit of Japanese Application No. 2010-048645 filed Mar. 5, 2010 in the Japanese Intellectual Property Office, the contents of both of which are incorporated herein by reference.

FIELD OF THE INVENTION

The present invention relates to a remote controlled actuator assembly capable of altering the attitude of an operating tool fitted to a tip end of an elongated guide section.

BACKGROUND ART

Remote controlled actuator assemblies are currently available; some are used for operations like cutting operations in, for example, the medical field or the mechanical processing field. Any of those remote controlled actuator assemblies controls by remote control an operating tool such as a machine tool or a holding tool that is fitted to a distal end of an elongated guide section of a linear or curved configuration. In the following description, conventional art and problems will be discussed with reference to remote controlled actuator assemblies in the medical field used for osteal treatment.

In orthopedics, the artificial joint replacement is well known, in which a joint, of which bone has been abraded by due to bone deterioration, is replaced with an artificial joint. The joint replacement surgery requires a living bone of a patient to be processed to enable an artificial joint to be implanted. In order to enhance the strength of postoperative adhesion between the living bone and the artificial joint, such processing is required to be performed precisely and accurately in conformity to the shape of the artificial joint.

By way of example, during the hip joint replacement surgery, a thigh bone is opened to secure access of an artificial joint into the femoral marrow cavity. In order to secure a strength of contact between the artificial joint and the bone, surfaces of contact of the artificial joint and the bore must be large and so the opening for insertion of the artificial joint is processed to represent an elongated shape extending deep into the bone. For such a processing, a remote controlled actuator assembly is used which is capable of rotating by remote control an operating tool fitted to a tip end of an elongated guide section. The surgical operation for artificial joint replacement generally accompanies skin incision and muscular scission. In other words, the human body must be invaded. In order to minimize the postoperative trace, it is quite often desirable that the elongated guide section referred to above is not necessarily straight, but is moderately curved.

To meet this desire, the following technique has hitherto been suggested. For example, the Patent Document 1 listed below discloses the guide section having its intermediate portion curved twice to displace an axial position of the distal end of the pipe relative to the longitudinal axis of the proximal end of the same pipe. To make the axial position of the distal end of the guide section displace relative to the longitudinal axis of the proximal end of the same guide section is also known from other publications. Also, the Patent Document 2 listed below discloses the guide section rotated by 180°.

PRIOR ART LITERATURE

[Patent Document 1] U.S. Pat. No. 4,466,429
[Patent Document 2] U.S. Pat. No. 4,265,231

Since such a conventional remote controlled actuator assembly is designed solely to control only the rotation of the machine tool by remote control, difficulties have been encountered in positioning the machine tool accurately in the distal deep site of the opening for insertion of the artificial joint or in processing a bone into a complex shape. One approach to overcoming such drawbacks was a configuration shown in FIG. 9A and FIG. 9B which includes a guide section 3 having a tip end to which a distal end member 2 is fitted for alteration in attitude, in which the distal end member 2 rotatably supports a machine tool 1 and in which the attitude of the distal end member 2 can be altered by remote control. More specifically, the guide section 3 has its interior a guide hole (not shown) having its opposite ends opening, within which an attitude altering member (not shown) is reciprocally movably inserted. The attitude of the distal end member 2 can be altered by applying an acting force via the attitude altering member to the distal end member 2 for alteration in attitude. A flexible attitude altering member such as a wire allows for such an acting force to be transmitted to the distal end member 2 for alteration in attitude, even when the guide section 3 and the guide hole in the interior of the guide section 3 are curved.

In such a remote controlled actuator assembly where an acting force is applied via an attitude altering member to the distal end member 2 for alteration in attitude, a preload applied in advance by the attitude altering member to the distal end member 2 keeps the attitude of the distal end member 2 stable. The preload is just enough to overcome possible external forces that the distal end member 2 may be subjected to. The alteration in attitude of the distal end member 2 is performed by advancing or retracting the attitude altering member according to the desired degree of alteration in attitude with respect to the initial position-attitude of the distal end member 2 and then applying the corresponding acting force to the distal end member.

In general, the initial position-attitude of the distal end member 2 is defined as the attitude of the distal end member 2 when the distal end member 2 is aligned straight with the guide section 3 as shown in FIG. 9B—that is, when the center line CL2 of the guide section 3 coincides with the center line CL1 of the distal end member 2. However, it is not unusual that the center line CL2 of the guide section 3 does not completely coincide with the center line CL1 of the distal end member 2, since factors such as processing accuracy and assembly accuracy of components may lead, when the components are assembled, to different remote controlled actuator assemblies having slightly different straightness of the distal end member 2 with respect to the guide section 3. Therefore, for each remote controlled actuator assembly, a reference position of an attitude altering member corresponding to the initial position-attitude of the distal end member 2 must be determined and the alteration in attitude of the distal end member 2 must be controlled based on the determined reference position, in order to accurately alter the attitude of the distal end member 2 into a target attitude.

SUMMARY OF THE INVENTION

An object of the invention is to provide a remote controlled actuator assembly which is capable of accurately altering by remote control the attitude of a distal end member mounted to a tip end of an elongated guide section with the distal end member supporting an operating tool, and which can perform control of alteration in attitude of the distal end member based on the initial position-attitude of the distal end member while accommodating possibly different initial position-attitudes of distal end members among different remote controlled actuator assemblies.

Another object of the invention is to provide a restraining tool which is easy to use but can reliably restrain the distal end member to align the distal end member straight with the guide section.

A remote controlled actuator assembly of the present invention includes a guide section of an elongated shape, a distal end member fitted to a tip end of the guide section for alteration in attitude, an operating tool provided in the distal end member, an operating tool drive source for driving the operating tool, an attitude altering drive source for altering the attitude of the distal end member, and an attitude control unit for controlling the attitude altering drive source. The guide section has its interior accommodating a drive shaft for transmitting a drive force of the operating tool drive source to the operating tool and guide hole having its opposite ends opening. In such a case, attitude altering member is reciprocally movably inserted within the guide hole for undergoing a reciprocating or retracting motion so as to alter the attitude of the distal end member, the attitude altering member being selectively advanced or retracted by the attitude altering drive source. Advance or retraction position detector operable to detect an advance or retraction position of the attitude altering member is provided. The attitude control unit uses information on an advance or retraction position of the attitude altering member corresponding to an initial position-attitude of the distal end member and that information is a detection value obtained by the advance or retraction position detector while the distal end member is being restrained to align straight with the guide section, during which the attitude altering member keeps applying a preload to the distal end member.

According to the above described construction, the operating tool provided in the distal end member performs a certain operation. In such case, when the attitude altering member is selectively advanced and retracted one at a time by the attitude altering drive source, the attitude altering member works on the distal end member to allow the attitude of the distal end member, fitted to the tip end of the guide section for alteration in attitude, to alter. The attitude altering drive source is provided at a position distant from the distal end member and the alteration of the attitude of the distal end member is carried out by remote control. Since the attitude altering member is passed through the guide hole, the attitude altering member can work on the distal end member properly at all time without being displaced in a direction transverse to the longitudinal direction thereof, and the operation to alter the attitude of the distal end member takes place accurately.

Factors such as processing accuracy and assembly accuracy of components may lead, when the components are assembled, to different remote controlled actuator assemblies having slightly different straightness of a distal end member with respect to a guide section. In other words, the initial position-attitude of the distal end member varies among different remote controlled actuator assemblies. To address this, the advance or retraction position detector detects an advance or retraction position of the attitude altering member, while the distal end member is restrained to align straight with the guide section and while the attitude altering member keeps applying a preload to the distal end member. Such a detection value obtained by the advance or retraction position detector is used as an advance or retraction position of the attitude altering member corresponding to an initial position-attitude of the distal end member, in order for the attitude control unit to perform control of the alteration in attitude of the distal end member. In this way, appropriate control of alteration in attitude of the distal end member can be performed while accommodating possibly different initial position-attitudes of distal end members among different remote controlled actuator assemblies.

In the present invention, a restraining tool may be provided which is removably fitted to an area extending from an outer periphery of a tip end portion of the guide section to an outer periphery of the distal end member, so as to restrain the distal end member such that the distal end member is aligned straight with the guide section.

For instance, the restraining tool may include an inner peripheral member configured to be placed on the area extending from an outer periphery of the tip end portion of the guide section to the outer periphery of the distal end member, and a tubular outer peripheral member configured to be placed on an outer periphery of the inner peripheral member. In such case, the inner peripheral member may include a plurality of split bodies circumferentially spaced apart from each other, and an outer peripheral surface of the inner peripheral member and an inner peripheral surface of the outer peripheral member may be in the form of tapers that match with each other and are formed with a male thread and a female thread, respectively, that threadingly engage with each other. A restraining tool according to this construction may be disposed so as to cover the area extending from an outer periphery of a tip end portion of the guide section to an outer periphery of the distal end member, and the outer peripheral member thereof may be rotated in such a direction that the male and female threads fasten with each other. This causes the outer peripheral member to axially move with respect to the inner peripheral member such that the outer peripheral member gets closer to the larger diameter side of the tapers. This results in the constriction of the diameter of the inner peripheral member, thereby causing the split bodies to be pressed against the tip end portion of the guide section as well as the distal end member. In this way, even when the center line of the distal end member is not aligned with the center line of the guide section, the distal end member can be restrained such that the center line of the distal end member and the center line of the guide section are aligned with each other, thereby keeping the distal end member straight with respect to the guide section.

In the present invention, preferably, the attitude altering drive source is driven by a predetermined magnitude of power to apply a predetermined preload via the attitude altering member to the distal end member while the restraining tool keeps restraining the distal end member, when the information on an advance or retraction position of the attitude altering member is obtained. A predetermined magnitude of power with which the attitude altering drive source is driven allows for performing, under fixed conditions, the detection of an advance or retraction position of the attitude altering member corresponding to the initial position-attitude of the distal end member, thereby resulting in highly accurate detection results.

In the present invention, preferably, a reference position memory is provided which is configured to store, as a reference position of the attitude altering member corresponding to the initial position-attitude of the distal end member, an advance or retraction position of the attitude altering member at which the attitude altering member stops due to a balance achieved between a force that acts on the distal end member from the attitude altering member and a reactive force from the distal end member. Also, preferably, an initial attitude controller is provided which is configured to perform control in such a way that the advance or retraction of the attitude altering member and the storage of the reference position of the attitude altering member in the reference position memory are carried out in successive actions. The provision of the reference position memory allows for storage of the reference position of the attitude altering member corresponding to the initial position-attitude of the distal end member. This allows for use of the reference position of the attitude altering member when altering the attitude of the distal end member, thereby enabling appropriate control of alteration in attitude of the distal end member based on the initial position-attitude thereof. Also, the provision of the initial attitude controller allows the operation of storing the reference position of the attitude altering member in the reference position memory to be automatically performed.

In the present invention, the distal end member may be fitted such that the attitude of the distal end member can be altered in an arbitrary direction with respect to the guide section, the guide hole as well as the attitude altering member inserted within the guide hole may be provided at three or more locations about a tilt axis of the distal end member, the attitude altering drive source may be provided separately with one for each of the attitude altering members, and the attitude of the distal end member can be altered and maintained in two axis-directions perpendicular to each other depending on the balance among the respective forces that the attitude altering members provided at three or more locations apply to the distal end member. A configuration in which the attitude of the distal end member can be altered and maintained in two axis-directions perpendicular to each other allows for the operating tool provided in the distal end member to be accurately positioned. Also, since the forces for altering and maintaining the attitude of the distal end member are provided by at least three attitude altering members, the attitude stability of the distal end member can be increased.

In such a configuration where the attitude of the distal end member can be altered by at least three attitude altering members in two axis-directions perpendicular to each other, preferably, for every combination of orders in which the attitude altering members provided at three or more locations can be advanced or retracted one by one, the attitude altering members are advanced or retracted one by one until an advance or retraction stop position is detected, the detected values for each of the attitude altering members are subject to a predetermined statistical processing procedure to obtain a statistically processed value for each of the attitude altering members, and the statistically processed value is used as a reference position of each of the attitude altering members corresponding to the initial position-attitude of the distal end member. The statistically processed value is, for example, an arithmetic average value of the detected values.

Such determination of the reference position of each of the attitude altering members minimizes possible deviation in the detected values among different orders in which the attitude altering members are operated, thereby providing more accurate value.

In the present invention according to any of the above constructions or configurations, the guide section may include a curve portion. In such a case, the attitude altering member may be flexible. This enables the attitude altering member to advance or retract in the guide hole, regardless of the presence of the curve portion in the guide section.

In the present invention, the restraining tool may be configured to restrain the distal end member such that the distal end member is aligned straight with the guide section, and may include: an inner peripheral member configured to be placed on an area extending from an outer periphery of a distal end portion of the guide section to an outer periphery of the distal end member; and a tubular outer peripheral member configured to be placed on an outer periphery of the inner peripheral member. In such case, the inner peripheral member may include a plurality of split bodies circumferentially spaced apart from each other, and an outer peripheral surface of the inner peripheral member and an inner peripheral surface of the outer peripheral member may be in the form of tapers that match with each other and are formed with a male thread and a female thread, respectively, that threadingly engage with each other. A restraining tool according to this construction may be disposed such that the split bodies of the inner peripheral member cover the area extending from an outer periphery of a tip end portion of the guide section to an outer periphery of the distal end member, and the outer peripheral member thereof may be rotated in such a direction that the male and female threads fasten with each other. This causes the outer peripheral member to axially move with respect to the inner peripheral member such that the outer peripheral member gets closer to the larger diameter side of the tapers. This results in the constriction of the diameter of the inner peripheral member, thereby causing the split bodies to be pressed against the tip end portion of the guide section as well as the distal end member. In this way, even when the center line of the distal end member is not aligned with the center line of the guide section, the distal end member can be restrained to align the center line of the distal end member with the center line of the guide section, thereby keeping, by simple procedures, the distal end member straight with respect to the guide section.

BRIEF DESCRIPTION OF THE DRAWINGS

In any event, the present invention will become more clearly understood from the following description of embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the different figures, and:

FIG. 1A shows a schematic construction of a remote controlled actuator assembly according to an embodiment of the present invention;

FIG. 1B shows a fragmentary view of the remote controlled actuator assembly in a different configuration;

FIG. 7 is the second flow chart for the initial attitude controller;

DESCRIPTION OF PREFERRED EMBODIMENTS

Figure 2A:
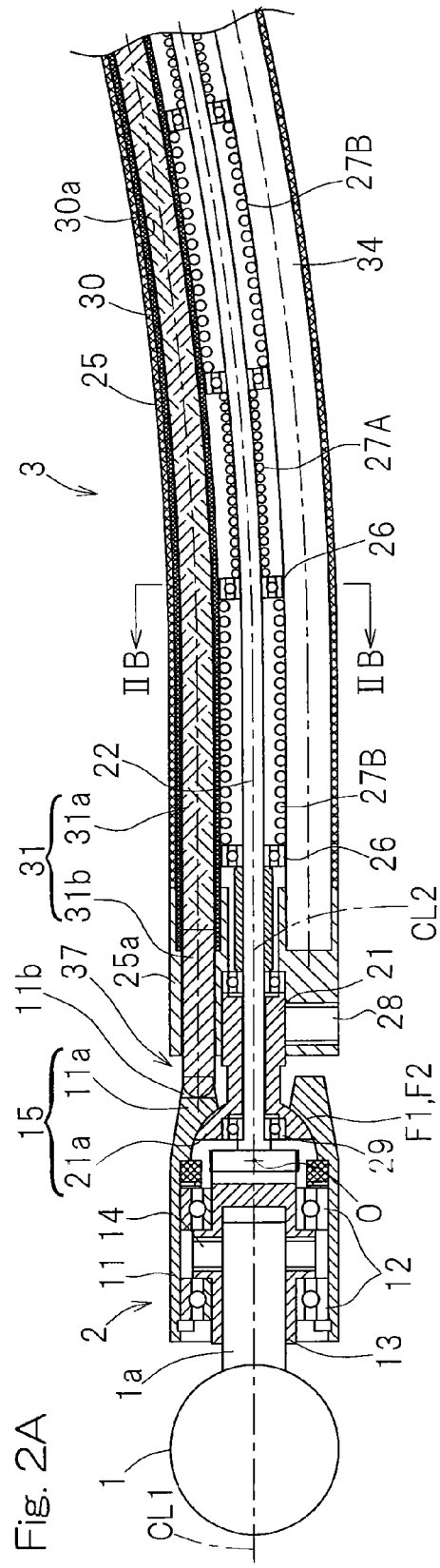
FIG. 2A shows a cross sectional view of a distal end member and a guide section of the remote controlled actuator assembly of FIG. 1A.
Figure 2D:
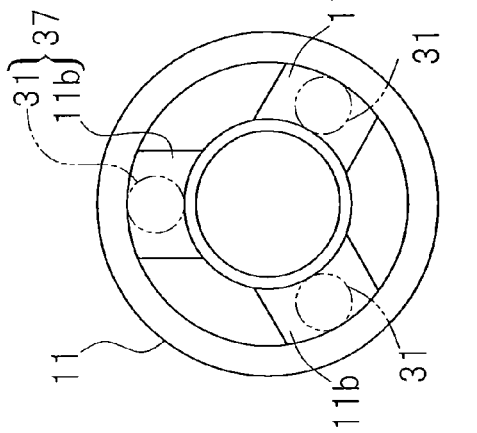
FIG. 2D shows a housing for the distal end member as viewed from a base end of the housing.

A remote controlled actuator assembly according to an embodiment of the present invention will be described in connection with FIGS. 1A and 1B through FIG. 7. As shown in FIG. 1A, the remote controlled actuator assembly includes an actuator body 5, a restraining tool 6 that is an accessory to the actuator body 5, and a controller 7 for controlling the actuator body 5. The actuator body 5 and the controller 7 are connected with each other via an electrical cable (not shown). Note that FIG. 1A shows an overall view of the remote controlled actuator assembly wherein the restraining tool 6 is not used, while FIG. 1B shows a fragmentary view of the remote controlled actuator assembly wherein the restraining tool 6 is used.

The actuator body 5 includes a distal end member 2 for holding an operating tool in the form of a rotary tool 1, a guide section 3 of an elongated, curved shape having a tip end to which the distal end member 2 is fitted for alteration in attitude, and a drive unit housing 4a to which a base end of the guide section 3 is connected. The drive unit housing 4a forms a drive unit 4 together with a built-in operating tool drive mechanism 4b and a similarly built-in attitude altering drive mechanism 4c. Although in the illustrated example the guide section 3 has an arcuate shape having a substantially constant curvature along its length, the guide section 3 may have a linear shape.

As shown in FIG. 2A to 2D, the distal end member 2 includes a generally or substantially cylindrical housing 11 and a spindle 13 rotatably accommodated within such cylindrical housing 11 through a pair of bearings 12. The spindle 13 is of a tubular shape having a distal side opening and has a hollow defined therein, and a tool 1 is drivingly coupled with the spindle 13. Specifically, a shank portion 1a of the tool 1 is inserted into the hollow of the spindle 13 and is then coupled with such spindle 13 by means of a stop pin 14 for rotation together with the spindle 13. The distal end member 2 of the structure described above is coupled with a distal end of the guide section 3 through a distal end member connecting unit 15. The distal end member connecting unit 15 supports the distal end member 2 for displacement in attitude and is comprised of a spherical bearing. More specifically, the distal end member connecting unit 15 includes a guided member 11a in the form of an inner diameter reduced portion at a base end of the housing 11, and a guide member 21a in the form of a collar integral with a constraint member 21 fixed to the tip of the guide section 3. The guided member 11a and the guide member 21a have respective guide faces F1 and F2 that are held in sliding contact with each other, and those guide faces F1 and F2 have respective centers of curvature lying at a point O on the center line or longitudinal axis CL1 of the distal end member 2, having their diameters being reduced towards the base end of the distal end member 2. Accordingly, not only can the distal end member 2 be immovably constrained relative to the guide section 3, but it can also be supported for displacement in attitude so that the attitude of the distal end member 2 can be altered in an arbitrary direction.

The guide section 3 includes a drive shaft 22 for transmitting a rotational force exerted by an operating tool drive source 41 (FIG. 1A, FIG. 3A and FIG. 3B) accommodated within the drive unit housing 4a. In the illustrated example, the drive shaft 22 is employed in the form of a wire capable of undergoing deformation to a certain extent. Material for the wire includes, for example, metal, resin or glass fiber. The wire may be either a single wire or a stranded wire. As best shown in FIG. 2C, the spindle 13 and the drive shaft 22 are coupled together by means of a joint 23 such as a universal joint for transmitting rotation from the rotary shaft 22 to the spindle 13. The joint 23 is made up of a groove 13a, defined in a closed base end of the spindle 13, and of a projection 22a defined in a distal end of the drive shaft 22 and engageable in the groove 13a. The center of joint between the groove 13a and the projection 22a is located at the same position as the centers of curvature O of the guide faces F1 and F2. Note that the drive shaft 22 and the projection 22a may be designed as members separate from each other.

The guide section 3 has an outer shell pipe 25, which forms an outer shell of the guide section 3, and the drive shaft 22 referred to above is positioned at a center of this outer shell pipe 25. The drive shaft 22 so positioned is rotatably supported by a plurality of rolling bearings 26 positioned spaced a distant apart from each other in a direction axially of the guide section 3. Between the neighboring rolling bearings 26, spring elements 27A for generating a preload on the inner rings of the corresponding rolling bearing 26 and spring elements 27B for generating the preload on the outer rings of the corresponding rolling bearings 26 are alternately disposed relative to each other. Those spring elements 27A and 27B may be employed in the form of, for example, compression springs. The constraint member 21 referred to previously is fixed to a pipe end portion 25a of the outer shell pipe 25 by means of a fixing pin 28 and has its distal end inner peripheral portion supporting a distal end of the drive shaft 22 through a rolling bearing 29. It is, however, to be noted that the pipe end portion 25a may be a member separate from the outer shell pipe 25 and may then be connected with the outer shell pipe 25 by means of, for example, welding.

Figure 2C:
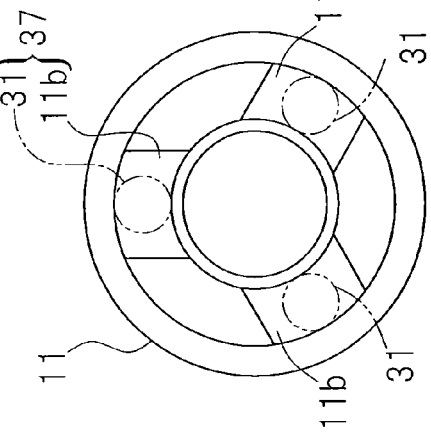
FIG. 2C shows a coupling configuration between the distal end member and a drive shaft.
Figure 2B:
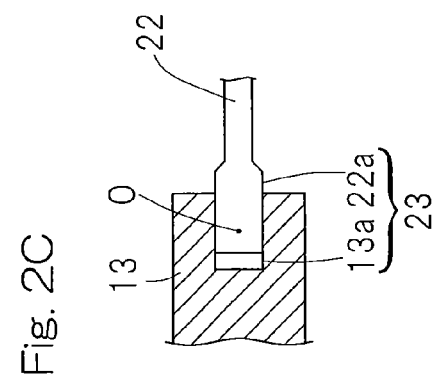
FIG. 2B shows a cross sectional view of FIG. 2A taken along the line IIB-IIB.

As shown in FIG. 2B, provided between an inner diametric surface of the outer shell pipe 25 and the drive shaft 22 are three guide pipes 30 each having its opposite ends opening and each having a curved shape similar to that of the outer shell pipe 25. The three guide pipes 30 are employed and arranged at respective circumferential locations spaced 120° in phase from each other, and the attitude altering member 31(31U, 31L, 31R) is reciprocally movably inserted in each of the guide holes 30a, which are inner diametric holes of such guide pipes 30. Each of the attitude altering members 31 is in the form of a wire 31a and pillar shaped pins 31b connected to opposite ends of the wire 31a. Material for the wire 31a includes, similarly to that of the drive shaft 22, metal, resin or glass fiber. The wire 31a may be either a single wire or a stranded wire. A shape memory alloy can be suitably employed therefor. One of the pillar shaped pins 31b that is closer to the distal end member 2 has a tip end representing a spherical shape which is held in contact with a bottom surface of a radial groove portion 11b formed in a base end surface of the housing 11. The groove portion 11b and one of the attitude altering members 31 form a rotation preventing mechanism 37, in which the distal end of the attitude altering member 31 inserted in the groove portion 11b comes in contact with the side surface of the groove portion 11b, thereby preventing the distal end member 2 from rotating with respect to the guide section 3 about the center line CL1 of the distal end member 2.

Also, a plurality of reinforcement shafts 34 are arranged, separate from the guide pipes 30, between the inner diametric surface of the outer shell pipe 25 and the drive shaft 22 and on the same pitch circle C as that depicted by the guide pipes 30. Those reinforcement shafts 34 are employed for securing the rigidity of the guide section 3. The reinforcement shafts 34 have the same outer diameter as the guide pipes 30 and each of them has a curved shape similar to those of the guide pipes 30. The guide pipes 30 and the plural reinforcement shafts 34 are spaced an equal distance from each other. The guide pipes 30 and the plural reinforcement shafts 34 are held in contact with the inner diametric surface of the outer shell pipe 25 and an outer diametric surface of each of the rolling bearings 26 so as to support the respective outer diametric surfaces of the rolling bearings 26.

Figure 3A:
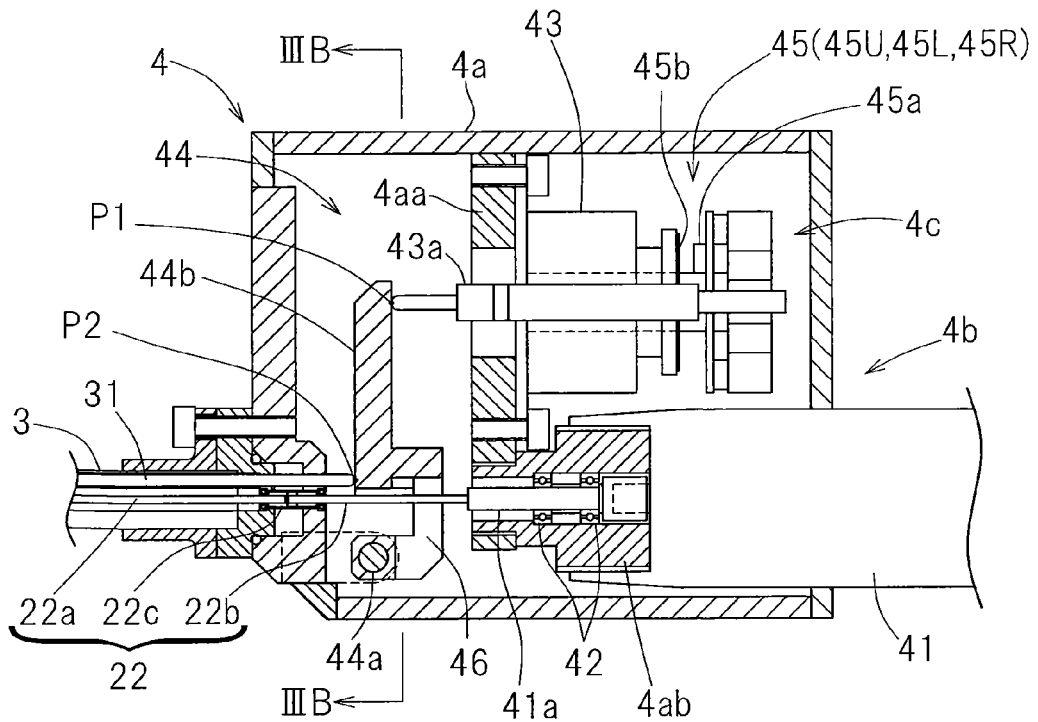
FIG. 3A shows a cross sectional view of an operating tool drive mechanism and an attitude altering drive mechanism of the remote controlled actuator assembly.
Figure 3B:
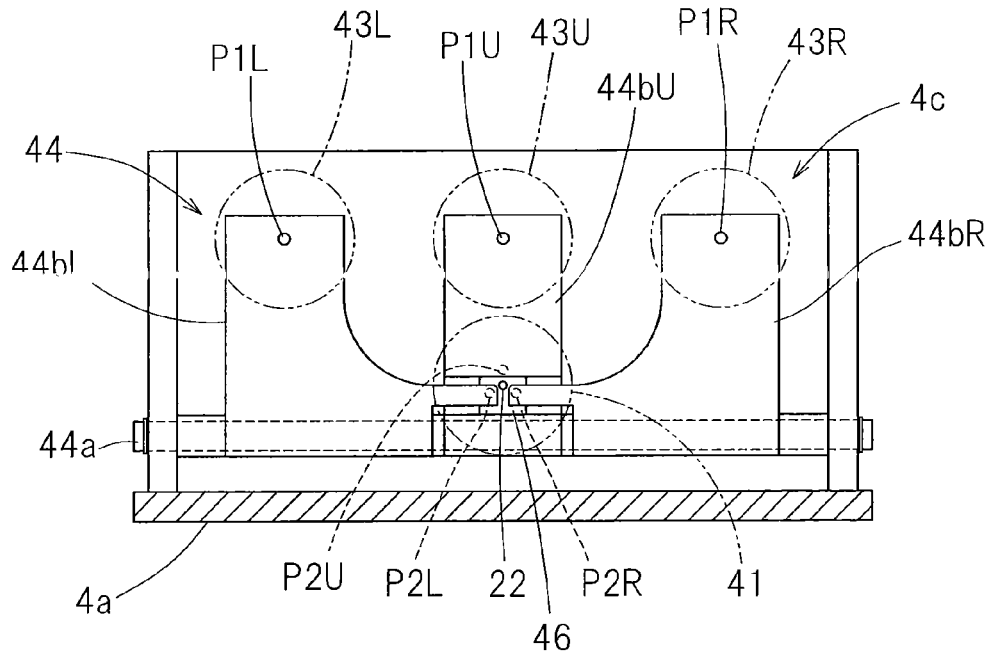
FIG. 3B shows a cross sectional view of FIG. 3A taken along the line IIIB-IIIB.

FIG. 3A shows an enlarged cross sectional view of the drive unit 4, and FIG. 3B shows a cross sectional view taken along the line IIIB-IIIB of FIG. 3A. As shown in FIG. 3A, the operating tool drive mechanism 4b includes an operating tool drive source 41 that is in the form of, for example, an electrically-driven motor. The operating tool drive source 41 is supported by the drive unit housing 4a, having an interior wall 4aa, and by a support member 4ab attached to the interior wall 4aa, such that the rear portion of the operating tool drive source 41 protrudes from the drive unit housing 4a to the outside. The output shaft 41a of the operating tool drive source 41 is rotatably supported by the support member 4ab through rolling contact bearings 42. The tip end of the output shaft 41a is connected with the proximal end of the drive shaft 22. It is to be noted that the drive shaft 22 is comprised of a guide section inside portion 22a located inside of the guide section and a drive unit inside portion 22b located inside of the drive unit, with the portions 22a, 22b being coupled with each other by a coupling 22c.

As shown in FIG. 3B, the attitude altering drive mechanism 4c includes attitude altering drive sources 43(43U, 43L, 43R) that correspond to respective attitude altering members 31(31U, 31L, 31R) shown in FIG. 2B. Each of the attitude altering drive sources 43 is attached to the interior wall 4aa. Each of the attitude altering drive sources 43 is in the form of, for example, an electrically-driven linear actuator. The movement of an output rod 43a of each of the attitude altering drive sources 43 in directions that are left and right as viewed on FIG. 3A is transmitted via a force amplification and transmission mechanism 44 to the corresponding attitude altering member 31. The operational position of the output rod 43a, that is, the advance or retraction position of the attitude altering member 31 is detected by an advance or retraction detector 45(45U, 45L, 45R). The advance or retraction detector 45 is in the form of, for example, an optical rotation sensor 45a that measures the amount of advance or retraction of the output rod 43a from the amount of rotation of a to-be-detected portion 45b disposed at a rotational member of the attitude altering drive source 43.

The force amplification and transmission mechanism 44 includes a pivot lever 44b(44bU, 44bL, 44bR) pivotable about a support pin 44a and is so designed and so configured as to allow a force of the output rod 43a to work on a working point P1(P1U, P1L, P1R) of the corresponding lever 44b, which is spaced a long distance from the support pin 44a, and as to apply a force to a corresponding attitude altering member 31 at a force point P2(P2U, P2L, P2R), which is spaced a short distance from the support pin 44a, wherefore the output of the corresponding attitude altering drive source 43 can be increased and then transmitted to the corresponding attitude altering member 31. The provision of the force amplification and transmission mechanism 44 enables a linear actuator having a small output to apply a large force to the attitude altering member 31, making it possible to reduce the size of the linear actuator. The drive shaft 22 referred to above is made to extend through an opening 46 defined in the pivot lever 44b.

Figure 4A:
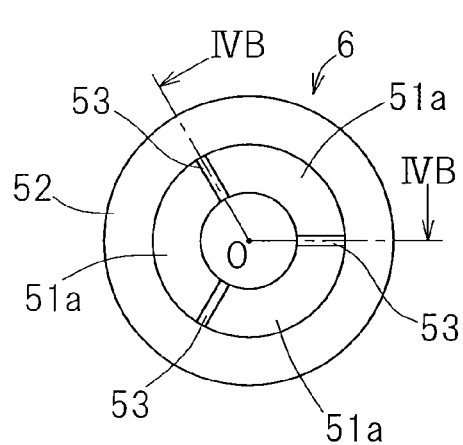
FIG. 4A shows a front elevational view of a restraining tool for the remote controlled actuator assembly.
Figure 4B:
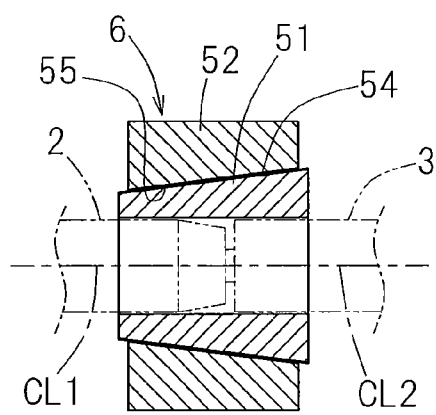
FIG. 4B shows a cross sectional view of the restraining tool taken along IVB-O-IVB.

The restraining tool 6 is used to retrain the distal end member 2 such that the distal end member 2 is aligned straight with the guide section 3. As shown in FIG. 4A and FIG. 4B, the restraining tool 6 includes an inner peripheral member 51 and an outer peripheral member 52. The inner peripheral member 51 is divided into a plurality of split bodies 51a circumferentially spaced apart from each other. The inner diameter of the inner peripheral member 51 is chosen such that the inner peripheral member 51 fits to an outer periphery of the distal end member 2 and to an outer periphery of the guide section 3. When the inner peripheral member 51 is fitted in such a manner, a circumferential gap 53 will be created between the split bodies 51a. An outer peripheral surface of each of the split bodies 51a is in the form of a taper. The outer peripheral surface in the form of such a taper is formed with a male thread 54 extending over the split bodies 51a. The outer peripheral member 52 is also in the form of a taper which matches with the outer peripheral surface of the inner peripheral member 51. The inner peripheral surface in the form of such a taper is formed with a female thread 55 that threadingly engages with the male thread 54.

With the threads 54, 55 of the inner and outer peripheral members 51, 52 being loosely engaged with each other, the restraining tool 6 is disposed so as to cover an area extending from an outer periphery of a tip end portion of the guide section 3 to an outer periphery of the distal end member 2, and the outer peripheral member 52 is rotated in such a direction that the threads 54, 55 fasten with each other. This causes the outer peripheral member 52 to axially move with respect to the inner peripheral member 51 such that the outer peripheral member 52 gets closer to the larger diameter side of the tapered surfaces. This results in the constriction of the diameter of the inner peripheral member 51, thereby causing the split bodies 51a to be pressed against the distal end portion of the guide section 3 and the distal end member 2. In this way, even when the center line CL1 of the distal end member 2 is not aligned with the center line CL2 of the guide section 3, the distal end member 2 can be restrained to align the center line CL1 of the distal end member 2 with the center line CL2 of the guide section 3, thereby keeping, by simple procedures, the distal end member 2 straight with respect to the guide section 3 such as shown in FIG. 4B.

Figure 5:
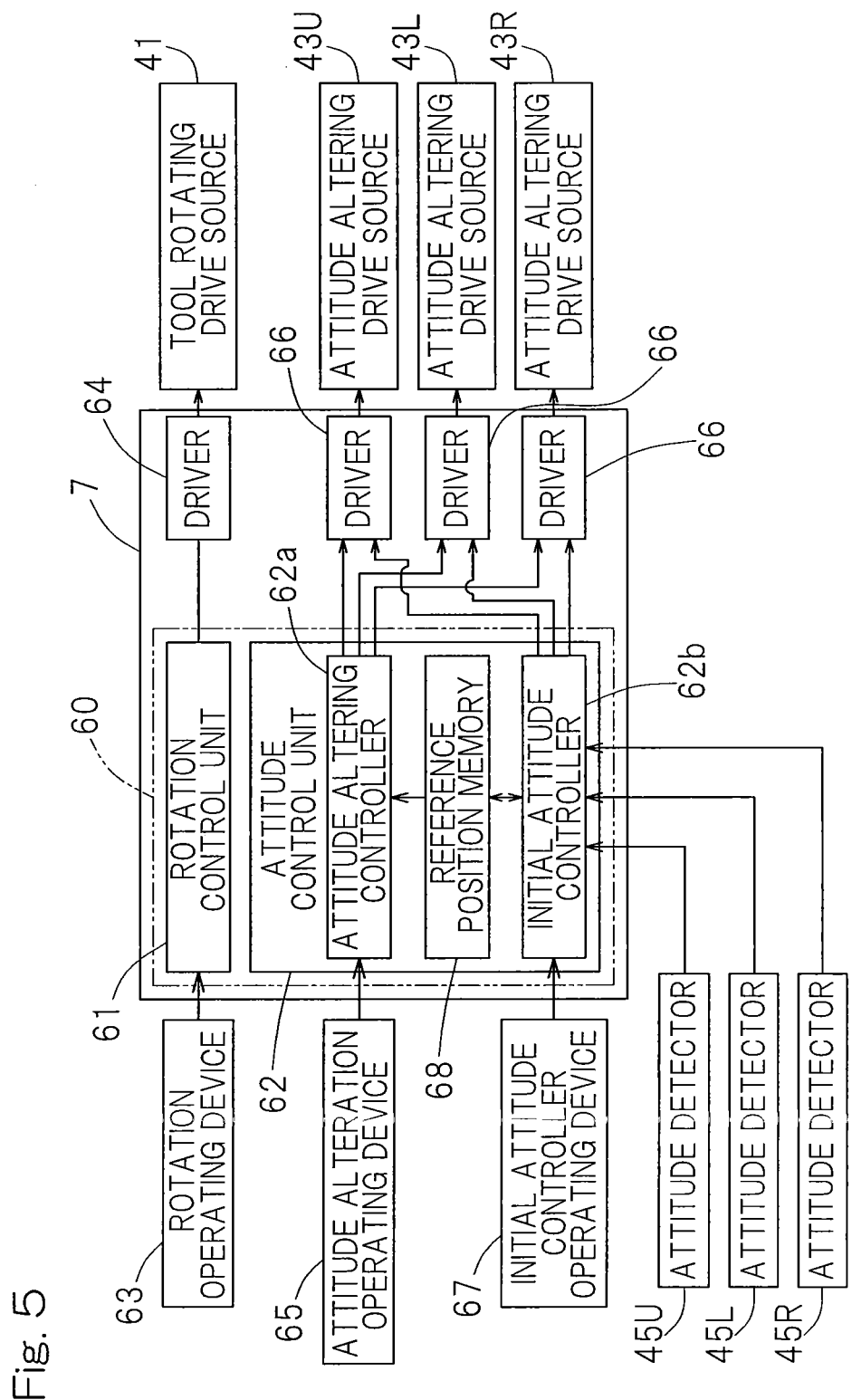
FIG. 5 shows a block diagram of a schematic configuration of a control system of the remote controlled actuator assembly.

As shown in FIG. 5, the controller 7 is built-in with a computer 60 that performs a variety of controls. The computer 60 includes a rotation control unit 61 configured to control the operating tool drive source 41 and an attitude control unit 62 configured to control the attitude altering drive sources 43(43U, 43L, 43R). The attitude control unit 62 includes an attitude altering controller 62a and an initial attitude controller 62b.

The rotation control unit 61 switches on/off the operating tool drive source 41 by generating an output to a driver 64 in response to a rotation command signal from a rotation operating device 63. In this way, the spindle 13 is caused to rotate or to stop rotating. The rotation operating device 63 may be included in the controller 7 or disposed in or on the drive unit housing 4a.

The attitude altering controller 62a of the attitude control unit 62 drives the attitude altering drive sources 43 by generating an output to the drivers 66 in response to an attitude altering command signal from an attitude alteration operating device 65. The attitude alteration operating device 65 can perform an operation of altering the attitude of the distal end member 2 in two axis-directions perpendicular to each other—namely, x-direction and y-direction of FIG. 2B—and can also perform the setting of the degree of that alteration in attitude. The attitude alteration operating device 65 may be included in the controller 7 or disposed in or on the drive unit housing 4a.

For example, to alter the attitude of the distal end member 2 such that the tip end of the distal end member 2 gets oriented downwardly in FIG. 2A, the restraining tool 6 is removed and the attitude altering member 31U on the upper side as shown in FIG. 2B is advanced towards the distal, tip end side while the other two attitude altering members 31L, 31R are retracted, by generating an output to each of the attitude altering drive sources 43U, 43L, 43R. As a result, the housing 11 for the distal end member 2 is pressed by the upper attitude altering member 31U to allow the distal end member 2 to be altered in attitude along the guide surfaces F1 and F2 with the tip end side oriented downwardly. At this time, those attitude altering drive sources 43 are controlled so that the amount of advance or retraction of each of the attitude altering members 31 may become proper. On the other hand, when each of those attitude altering members 31 is retracted or advanced conversely to what has just been discussed, the housing 11 for the distal end member 2 is pressed by the attitude altering members 31L and 31R, which are shown on lower left and lower right sides, and, consequently, the distal end member 2 is altered in attitude along the guide surfaces F1 and F2 with the tip end side oriented upwardly.

Also, to alter the attitude of the distal end member 2 such that the tip end of the distal end member 2 gets oriented rightwards or towards a 180 degree inverted side (a rear side of the sheet of the drawing of FIG. 2A), the attitude altering member 31U on the upper side is held still, and the attitude altering member 31L on the left side is advanced towards the tip end side while the attitude altering member 31R on the right side is retracted, by generating an output to each of the attitude altering drive sources 43L, 43R. As a result, the housing 11 for the distal end member 2 is pressed by the attitude altering member 31L on the left side to allow the distal end member 2 to be altered in attitude along the guide surfaces F1 and F2 with the distal end member 2 oriented rightwards. On the other hand, when the attitude altering members 31L and 31R on the left and right sides are advanced and retracted conversely to what has just been discussed, the housing 11 for the distal end member 2 is pressed by the attitude altering member 31R on the right side, allowing the distal end member 2 to be altered in attitude so that the distal end member 2 can be guided along the guide surfaces F1 and F2 so as to be oriented leftwards.

The initial attitude controller 62b of the attitude control unit 62, upon the completion of assembly of a remote controlled actuator assembly or upon the replacement of the distal end member 2, carries out an initial attitude control which includes detecting and storing a reference position that is an advance or retraction position of each of the attitude altering members 31 corresponding to the initial position-attitude of the distal end member 2. An initial position-attitude of the distal end member 2 is defined as the attitude of the distal end member 2 when the distal end member 2 is aligned straight with the guide section 3—that is, when the center line CL2 of the guide section 3 coincides with the center line CL1 of the distal end member 2. A remote controlled actuator assembly should be designed such that the center line CL1 of the distal end member 2 coincides with the center line CL2 of the guide section 3 when all of the attitude altering drive sources 43 are in respective neutral positions with the tip end of each of the attitude altering members 31 being in contact with the housing 11 for the distal end member 2. However, it is not unusual that the center line CL2 of the guide section 3 does not completely coincide with the center line CL1 of the distal end member 2 as shown in FIG. 1A, since factors such as processing accuracy and assembly accuracy of components may lead, when the components are assembled, to different remote controlled actuator assemblies having slightly different straightness of the distal end member 2 with respect to the guide section 3. Therefore, for each remote controlled actuator assembly, a reference position of each of attitude altering members 31 corresponding to the initial position-attitude of the distal end member 2 is determined to decide the output of each of the attitude altering drive sources 43 based on the determined reference position, so that the attitude of the distal end member 2 can be accurately altered into a target attitude.

The initial attitude controller 62b is connected with an initial attitude controller operating device 67 and a reference position memory 68. The initial attitude controller operating device 67 is an operating device that causes an initial attitude control, which will be described in detail later, to be carried out. The reference position memory 68 is a rewritable memory.

To carry out an initial attitude control, firstly, the distal end member 2 is restrained by means of the restraining tool 6 such the distal end member 2 is aligned straight with respect to the guide section 3, as shown in FIG. 1B. If the distal end member 2 is fixedly positioned at an angle with respect to the guide section 3 due to a preload between the distal end member 2 and the attitude altering members 31, the attitude altering members 31 are retracted to allow the distal end member 2 to be freely altered in attitude, before restraining the distal end member 2 by means of the restraining tool 6.

Figure 6:
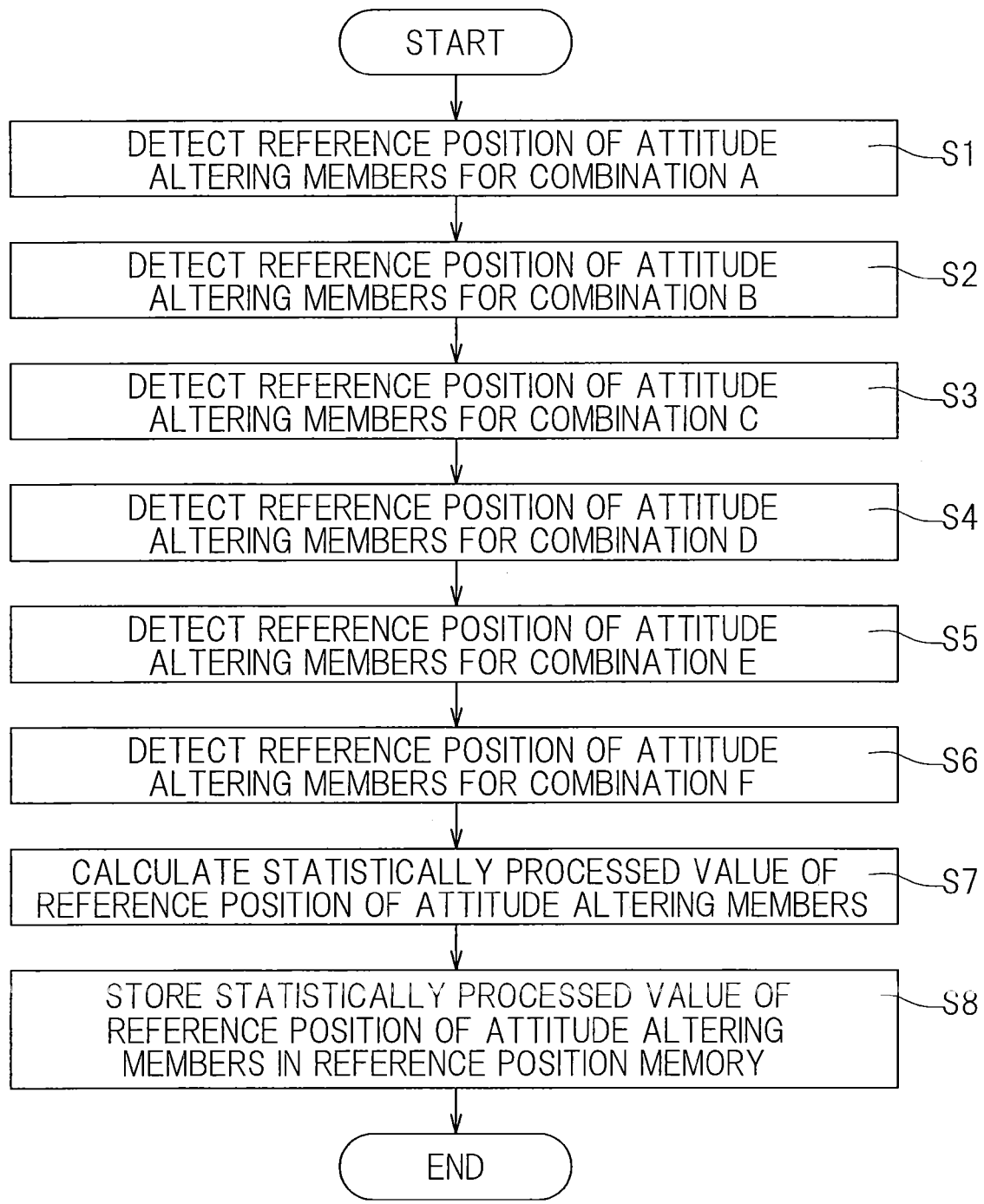
FIG. 6 is the first flow chart for an initial attitude controller.

The initial attitude controller will be described in detail in connection with the flow charts shown in FIG. 6 and FIG. 7, using as an example a case in which the reference position of each of the attitude altering members 31U, 31L, 31R is obtained by advancing or retracting the attitude altering members 31U, 31L, 31R according to the combination of orders as illustrated in Table 1. The initial attitude controller starts by operating the initial attitude controller operating device 67.

TABLE 1

| Combination | First | Second | Third |
| --- | --- | --- | --- |
| A | Attitude altering member on the upper side | Attitude altering member on the left side | Attitude altering member on the right side |
| B | Attitude altering member on the upper side | Attitude altering member on the right side | Attitude altering member on the left side |
| C | Attitude altering member on the left side | Attitude altering member on the upper side | Attitude altering member on the right side |
| D | Attitude altering member on the left side | Attitude altering member on the right side | Attitude altering member on the upper side |

TABLE 1-continued

| Combination | First | Second | Third |
|---|---|---|---|
| E | Attitude altering member on the right side | Attitude altering member on the upper side | Attitude altering member on the left side |
| F | Attitude altering member on the right side | Attitude altering member on the left side | Attitude altering member on the upper side |

Firstly, a reference position of the attitude altering members 31U, 31L, 31R for the combination A is obtained (S1). The detection procedures are described in FIG. 7; the attitude altering member 31U on the upper side is advanced by the attitude altering drive source 43U with a given predetermined magnitude of power, thereby causing the attitude altering member 31U to push the distal end member 2 (S101). The distal end member 2, which is retrained by the restraining tool 6, cannot be altered in attitude; and instead, a preload accumulates. As the preload reaches a certain magnitude and a balance is achieved between the reactive force from the distal end member 2 and the thrust force of that attitude altering member 31, that attitude altering member 31 gets prevented from advancing any longer (S102). The value detected for this particular moment by the corresponding advance or retraction detector 45U is temporarily stored (S103). Subsequently, the detection and the storage of a reference position of the attitude altering member 31L on the left side and of the attitude altering member 31R on the right side are carried out in a similar fashion (S104 through S109). Then, the attitude altering members 31U, 31L, 31R are retracted for the next rounds of procedures (S110).

In a similar manner to what has just been discussed for the combination A, a reference position of the attitude altering members 31U, 31L, 31R for the combinations B to F is detected and temporarily stored (S2 through S6). Then, the six sets of detected values obtained for the attitude altering members 31U, 31L, 31R from the combinations A to F are subject to a statistical processing procedure to obtain statistically processed values for the respective attitude altering members 31U, 31L, 31R (S7). The statistically processed values are stored in the reference position memory 68 (S8). Each of the statistically processed values is, for example, an arithmetic average value of each set of the detected values. Each of the statistically processed values may be an average of the remaining values after the maximum and minimum values are removed. Also, each of the statistically processed values may be a median of each set of the detected values.

Such successive procedures or actions are automatically performed by the initial attitude controller 62b. A given predetermined magnitude of power with which each of the attitude altering drive sources 43 is driven allows for performing, under fixed conditions, the detection of the advance or retraction position of each of the attitude altering members 31 corresponding to the initial position-attitude of the distal end member 2, thereby resulting in highly accurate detection results.

The values stored in the reference position memory 68 in the above discussed manner are used as the advance or retraction position of each of the attitude altering members 31 corresponding to the initial position-attitude of the distal end member 2, in order for the attitude altering controller 62a to perform control of alteration in attitude of the distal end member 2. In this way, appropriate control of alteration in attitude of the distal end member 2 can be performed while accommodating possibly different initial position-attitudes of distal end members 2 among different remote controlled actuator assemblies.

An operation of the remote controlled actuator assembly will now be described.

When the tool rotating drive source 41 is driven by operating the rotation operating device 63, the rotational force thereof is transmitted to the spindle 13 through the drive shaft 22 to thereby rotate the tool 1 together with the spindle 13. The tool 1 then being rotated cuts a bone or the like. During such processing, according to the shape of the site to be processed and/or the progression of the processing, the attitude of the distal end member 2 is altered in two axis-directions perpendicular to each other through the attitude altering members 31, by operating the attitude alteration operating device 65 and driving the attitude altering drive sources 43.

The attitude altering drive sources 43 are provided at a position distant from the distal end member 2 and the alteration of the attitude of the distal end member 2 is carried out by remote control. Since the attitude altering members 31 are inserted through the guide holes 30a, the attitude altering members 31 can properly act on the distal end member 2 at all times without being accompanied by displacement in position in a direction perpendicular to the lengthwise direction thereof and the attitude altering operation of the distal end member 2 can therefore be performed accurately. Also, since the center of the junction between the spindle 13 and the drive shaft 22 lies at the same position as the respective centers of curvature O of the guide faces F1 and F2, no force tending to press and pull will not act on the drive shaft 22 as a result of the alteration of the attitude of the distal end member 2 and the distal end member 2 can be smoothly altered in attitude.

Also, even in the case that the distal end member 2 for holding the tool 1 becomes out of control due to, for example, the failure of the attitude altering drive mechanism 4c and/or the attitude control unit 62, the rotation preventing mechanism 37, which prevents the distal end member 2 from rotating with respect to the guide section 3 about the center line CL1 of the distal end member 2, in turn, prevents the distal end member 2 from undesirably rotating about the center line CL1 and damaging the neighboring portions of the processing cite and/or from damaging and breaking itself.

The remote controlled actuator assembly of the foregoing construction is utilized in grinding the femoral marrow cavity during, for example, the artificial joint replacement surgery and during the surgery, it is used with the distal end member 2 in its entirety or a part thereof inserted into the body of a patient. Because of this, with such distal end member 2 as described above that can be altered in attitude by remote control, the bone can be processed in a condition with the tool 1 maintained in a proper attitude at all times and the opening for insertion of the artificial joint can be finished accurately and precisely.

There is the necessity that the drive shaft 22 and the attitude altering member 31 are provided within the guide section 3 of an elongated shape in a protected fashion. Hence, the drive shaft 22 is provided in the center portion of the outer shell pipe 25 and the guide pipes 30, in which the respective attitude altering members 31 are accommodated, and the reinforcement shafts 34 are arranged between the outer shell pipe 25 and the drive shaft 22 so as to be juxtaposed in the circumferential direction. Accordingly, it is possible to protect the drive shaft 22 and the attitude altering members 31 and, at the same time, the interior can be made hollow to thereby reduce the weight without sacrificing the rigidity. Also, the balance as a whole is good.

Since the outer diametric surfaces of the rolling bearings 26 supporting the drive shaft 22 are supported by the guide pipes 30 and the reinforcement shafts 34, the outer diametric surfaces of the rolling bearings 26 can be supported with no need to use any extra member. Also, since the preload is applied to the rolling bearings 26 by means of the spring elements 27A and 27B, the drive shaft 22 comprised of the wire can be rotated at a high speed. Because of that, the processing can be accomplished with the spindle 13 rotated at a high speed and a good finish of the processing can also be obtained and the cutting resistance acting on the tool 1 can be reduced. Since the spring elements 27A and 27B are disposed between the neighboring rolling bearings 26, the spring elements 27A and 27B can be provided with no need to increase the diameter of the guide section 3.

Figure 8A:
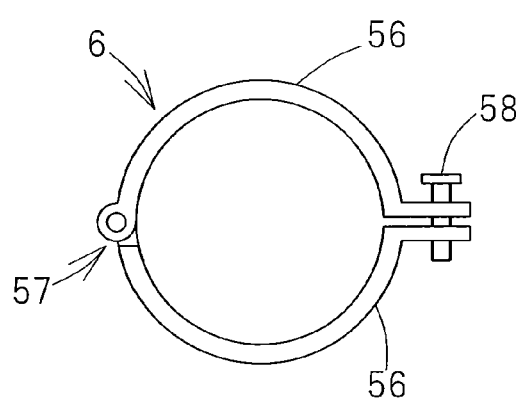
FIG. 8A shows a front elevational view of a different restraining tool.
Figure 8B:
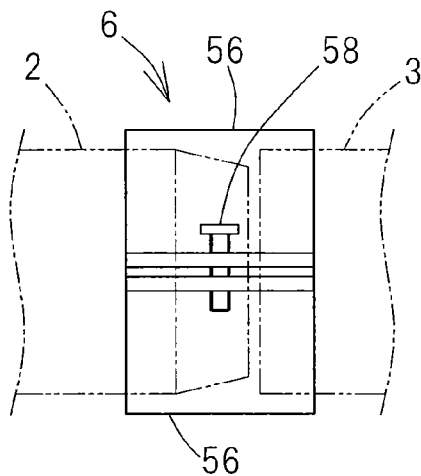
FIG. 8B shows a side view of the different restraining tool of FIG. 8A.
Figure 9A:
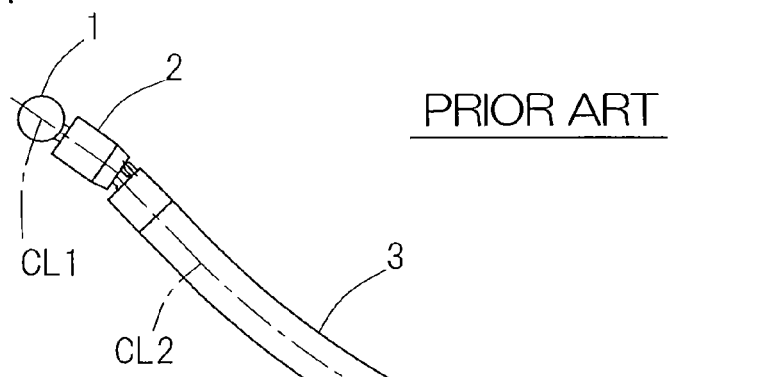
FIG. 9A shows a view for explaining an initial position-attitude of a distal end member.
Figure 9B:
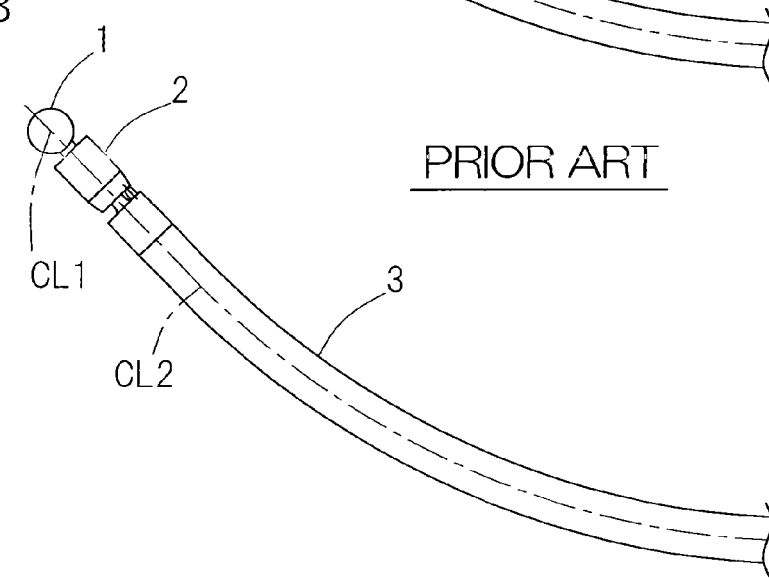
FIG. 9B shows a view for explaining the initial position-attitude of the distal end member in a different configuration.

The restraining tool 6 may have a configuration different from that shown in FIG. 4A and FIG. 4B. For instance, a restraining tool 6 as shown in FIG. 8A and FIG. 8B includes a pair of half members 56 each having a shape of a halved cylinder that is halved along the plane containing an axis of the cylinder. Each of the pair of the half members 56 has first and second ends, and the pair of the half members 56 are rotatably coupled with each other by a hinge 57 at their first ends, with their other second ends being fixable with each other by a bolt 58. The half members 56 are disposed so as to cover an area extending from an outer periphery of a tip end portion of the guide section 3 to an outer periphery of the distal end member 2 as shown in FIG. 8B, and then their second ends are clampingly fastened with each other by the bolt 58. As a result, the half members 56 are caused to be pressed against the tip end portion of the guide section 3 and the distal end member 2. In this way, the distal end member 2 can be restrained to align the center line CL1 of the distal end member 2 with the center line CL2 of the guide section 3, thereby keeping the distal end member 2 straight with respect to the guide section 3. Devices other than the restraining tool 6 may be used to restrain the distal end member 2 so as to keep the distal end member 2 straight with respect to the guide section 3.

In the embodiments that have been discussed above, the operating tool was shown and described as a rotary tool 1. However, the operating tool may be other type of operating tools such as a holding tool. Also, the present invention is not limited to a remote controlled actuator assembly for medical use, but may also be applied to remote controlled actuator assemblies used for other fields such as a machining field.

Although the present invention has been fully described in connection with the embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE SIGNS

1: TOOL (OPERATING TOOL)
2: DISTAL END MEMBER
3: GUIDE SECTION
4a: DRIVE UNIT HOUSING
6: RESTRAINING TOOL
22: DRIVE SHAFT
30: GUIDE PIPE
30a: GUIDE HOLE
31: ATTITUDE ALTERING MEMBER
41: OPERATING TOOL DRIVE SOURCE
43: ATTITUDE ALTERING DRIVE SOURCE
45: ADVANCE OR RETRACTION DETECTOR
51: INNER PERIPHERAL MEMBER
51a: SPLIT BODY
52: OUTER PERIPHERAL MEMBER
54: MALE THREAD
55: FEMALE THREAD
62: ATTITUDE CONTROL UNIT
62b: INITIAL ATTITUDE CONTROLLER

What is claimed is:

1. A remote controlled actuator assembly which comprises:

a guide section of an elongated shape;

a distal end member fitted to a tip end of the guide section for alteration in attitude;

an operating tool provided in the distal end member;

an operating tool drive source for driving the operating tool;

an attitude altering drive source for altering the attitude of the distal end member;

an attitude control unit for controlling the attitude altering drive source; and a restraining tool removably fitted to an area extending from an outer periphery of a tip end portion of the guide section to an outer periphery of the distal end member, so as to restrain the distal end member such that the distal end member is aligned straight with the guide section, in which the restraining tool includes an inner peripheral member configured to be placed on the area extending from an outer periphery of the tip end portion of the guide section to the outer periphery of the distal end member, and a tubular outer peripheral member configured to be placed on an outer periphery of the inner peripheral member;

in which the inner peripheral member includes a plurality of split bodies circumferentially spaced apart from each other, in which an outer peripheral surface of the inner peripheral member and an inner peripheral surface of the outer peripheral member are in the form of tapers that match with each other and are formed with a male thread and a female thread, respectively, that threadingly engage with each other, in which the guide section has its interior accommodating a drive shaft for transmitting a drive force of the operating tool drive source to the operating tool and a guide hole having its opposite ends opening, in which an attitude altering member is reciprocally movably inserted within the guide hole for undergoing a reciprocating or retracting motion so as to alter the attitude of the distal end member, the attitude altering member being selectively advanced or retracted by the attitude altering drive source, in which an advance or retraction position detector operable to detect an advance or retraction position of the attitude altering member is provided, and in which the attitude control unit uses information on an advance or retraction position of the attitude altering member corresponding to an initial position-attitude of the distal end member and that information is a detection value obtained by the advance or retraction position detector while the distal end member is being restrained to align straight with the guide section, during which the attitude altering member keeps applying a preload to the distal end member.

2. The remote controlled actuator assembly as claimed in claim 1, wherein the attitude altering drive source is driven by a predetermined magnitude of power to apply a predetermined preload via the attitude altering member to the distal end member while the restraining tool keeps restraining the distal end member, when the information on an advance or retraction position of the attitude altering member is obtained.

3. The remote controlled actuator assembly as claimed in claim 2, further comprising a reference position memory configured to store, as a reference position of the attitude altering member corresponding to the initial position-attitude of the distal end member, an advance or retraction position of the attitude altering member at which the attitude altering member stops due to a balance achieved between a force that acts on the distal end member from the attitude altering member and a reactive force from the distal end member.

4. The remote controlled actuator assembly as claimed in claim 3, further comprising an initial attitude controller configured to perform control in such a way that the advance or retraction of the attitude altering member and the storage of the reference position of the attitude altering member in the reference position memory are carried out in successive actions.

5. The remote controlled actuator assembly as claimed in claim 1, wherein the distal end member is fitted such that the attitude of the distal end member can be altered in an arbitrary direction with respect to the guide section,
the guide hole as well as the attitude altering member inserted within the guide hole are provided at three or more locations about a tilt axis of the distal end member,
the attitude altering drive source is provided separately with one for each of the attitude altering members, and
the attitude of the distal end member can be altered and maintained in two axis-directions perpendicular to each other depending on the balance among the respective forces that the attitude altering members apply to the distal end member.

6. The remote controlled actuator assembly as claimed in claim 1, wherein the distal end member is fitted such that the attitude of the distal end member can be altered in an arbitrary direction with respect to the guide section,
the guide hole as well as the attitude altering member inserted within the guide hole are provided at three or more locations about a tilt axis of the distal end member,
the attitude altering drive source is provided separately with one for each of the attitude altering members, and
the attitude of the distal end member can be altered and maintained in two axis-directions perpendicular to each other depending on the balance among the respective forces that the attitude altering members apply to the distal end member;
in which, for every combination of orders in which the attitude altering members provided at three or more locations can be advanced or retracted one by one, the attitude altering members are advanced or retracted one by one until an advance or retraction stop position is detected, the detected values for each of the attitude altering members are subject to a predetermined statistical processing procedure to obtain a statistically processed value for each of the attitude altering members, and the statistically processed value is used as a reference position of each of the attitude altering members corresponding to the initial position-attitude of the distal end member.

7. The remote controlled actuator assembly as claimed in claim 6, wherein the statistically processed value is an arithmetic average value of the detected values.

8. The remote controlled actuator assembly as claimed in claim 1, wherein the guide section includes a curve portion.

9. A remote controlled actuator assembly which comprises:
a guide section of an elongated shape;
a distal end member fitted to a tip end of the guide section for alteration in attitude;
an operating tool provided in the distal end member;
an operating tool drive source for driving the operating tool;
an attitude altering drive source for altering the attitude of the distal end member;
an attitude control unit for controlling the attitude altering drive source; and
a restraining tool removably fitted to an area extending from an outer periphery of a tip end portion of the guide section to an outer periphery of the distal end member, so as to restrain the distal end member such that the distal end member is aligned straight with the guide section, the remote controlled actuator assembly being configured to restrain the distal end member such that the distal end member is aligned straight with the guide section,
in which the restraining tool comprises an inner peripheral member configured to be placed on the area extending from an outer periphery of the tip end portion of the guide section to the outer periphery of the distal end member, the inner peripheral member having a plurality of split bodies circumferentially spaced apart from each other and a tubular outer peripheral member configured to be placed on an outer periphery of the inner peripheral member,
in which an outer peripheral surface of the inner peripheral member and an inner peripheral surface of the outer peripheral member are in the form of tapers that match with each other and are formed with a male thread and a female thread, respectively, that threadingly engage with each other,
in which the guide section has its interior accommodating a drive shaft for transmitting a drive force of the operating tool drive source to the operating tool and a guide hole having its opposite ends opening,
in which an attitude altering member is reciprocally movably inserted within the guide hole for undergoing a reciprocating or retracting motion so as to alter the attitude of the distal end member, the attitude altering member being selectively advanced or retracted by the attitude altering drive source,
in which an advance or retraction position detector operable to detect an advance or retraction position of the attitude altering member is provided, and
in which the attitude control unit uses information on an advance or retraction position of the attitude altering member corresponding to an initial position-attitude of the distal end member and that information is a detection value obtained by the advance or retraction position detector while the distal end member is being restrained to align straight with the guide section, during which the attitude altering member keeps applying a preload to the distal end member.

* * * * *

UNITED STATES PATENT AND TRADEMARK OFFICE
CERTIFICATE OF CORRECTION

| | | |
|---|---|---|
| PATENT NO. | : 9,282,976 B2 | Page 1 of 1 |
| APPLICATION NO. | : 13/582819 | |
| DATED | : March 15, 2016 | |
| INVENTOR(S) | : Yukihiro Nishio et al. | |

It is certified that error appears in the above-identified patent and that said Letters Patent is hereby corrected as shown below:

On the title page,

Column 2 (item (56) (Foreign Patent Documents), Line 2:
Delete "3/2011" and insert -- 3/2010 --, therefor.

In the claims,

Claim 9, Column 18, Line 32:
Delete "other" and insert -- other, --, therefor.

Signed and Sealed this
Seventh Day of June, 2016

Michelle K. Lee
*Director of the United States Patent and Trademark Office*